United States Patent [19]
Jolicoeur et al.

[11] Patent Number: 6,054,571
[45] Date of Patent: Apr. 25, 2000

[54] DFT-A GENE, DIAGNOSTIC AND THERAPEUTIC USES THEREOF

[75] Inventors: Paul Jolicoeur, Outremont, Canada; Aurelio Balsalobre, Annemasse, France

[73] Assignee: Institut de Recherches Cliniques de Montreal, Montreal, Canada

[21] Appl. No.: 09/075,215

[22] Filed: May 11, 1998

[51] Int. Cl.$^7$ .............................. C07H 21/04; C07H 21/02
[52] U.S. Cl. ........................................ 536/23.5; 536/23.1
[58] Field of Search .................................... 536/23.1, 23.4

*Primary Examiner*—Paula K. Hutzell
*Assistant Examiner*—Lin Sun-Hoffman
*Attorney, Agent, or Firm*—Swabey Ogilvy Renault; France Côté

[57] ABSTRACT

The present invention relates to a novel gene regulated by FOS and RAS transforming pathways, which is identified as dft-A, and which comprises the sequence set forth in FIG. 3. There is also disclosed the novel dft-A protein and an antibody recognizing same. The present invention also relates to a diagnostic method of identifying dft-A mutations in cancer or other diseases in a biological sample of a patient, which comprises: a) subjecting DNA present in the patient's sample to gene sequencing; and b) comparing the sequenced DNA with the sequence of dft-A gene to identify dft-A mutations. The present invention also relates to a diagnostic method of identifying change in dft-A protein level in cancer or other diseases in a biological sample of a patient, which comprises: a)subjecting the patient's sample to the anti-dft-A antibody to form an antibody-dft-A protein complex; and b) detecting the antibody-dft-A protein complex to determine the dft-A protein level in the biological sample.

1 Claim, 7 Drawing Sheets

FIG. 2A
Kb  1 2 3 4 5 6 7 8 9 10 11 12 13 14
6-
2.3-
Phenotype        N  N  T  T  N  N  N  N  T  T  N  N  T  T
Relative expression 10 14 19 80  5  7  5  5 19 30 11  9  5  9
(Rat-1=1)
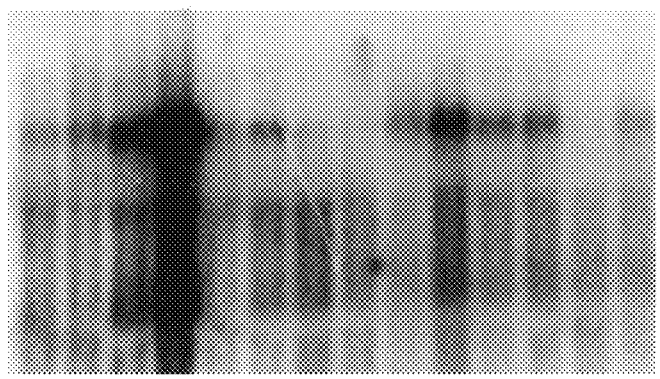
dft-C/cyr61-
FIG. 2B
Phenotype        N   N T  T  N  N  N  T  T  N  N  T  T
Relative expression 100 4 12 24 78 55 67 31  6  1  7 38 28 20
(Rat-1=1)
18S-
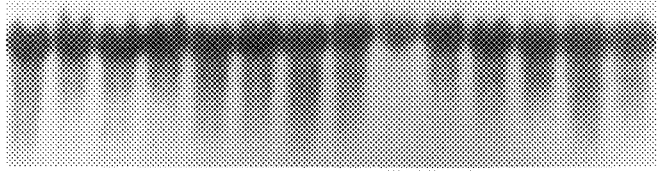
FIG. 2C

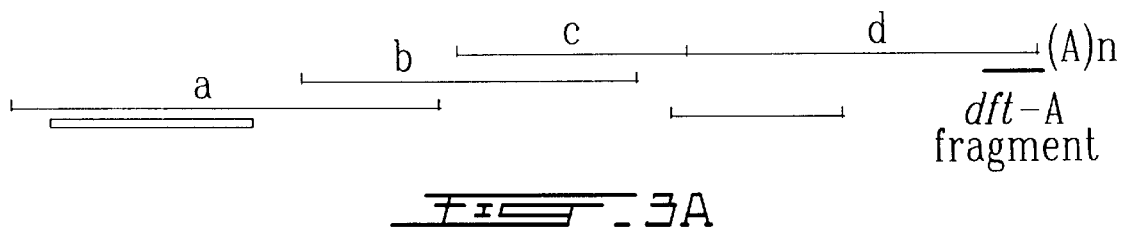

FIG. 3A

```
                                    ggaagctccggctcccggcggcggggctcgtaacccgcatcgagaagagg
cgcgggcggcggaggaggttggtacacgctcggtcctgcagagctccccgggtggccatggcgagaggtgcacggcgaccacccgagtggcg
cagcggtgtcagattcttcttgaacaagtaccaactccatggatccaggacaggtttgtcccatggcctgctctgagcagtgtgcagtctga
```

```
gagaagattccattggcaaaccatctctggccttacggaacaagcaaagacgATGGGTCTTCAGAAG       300
                                                   M  G  L  Q  K
         AGCCATCTGACTGTGTGTTTACCACCTTCTGTGCCCTTCTTAATCCTAGTATCCACTCTA        360
    6     S  H  L  T  V  C  L  P  P  S  V  P  F  L  I  L  V  S  T  L
         GCCACTGCTAAGAGTGTGACCAACAGCACTTTAAATGGCACTGATGTGGTCTTGGGCTCT        420
    26    A  T  A  K  S  V  T  N  S  T  L  N  G  T  D  V  V  L  G  S
         GTGCCCGTAATCATTGCCAGAACTGACCATATCATAGTCAAAGAGGGGAGCAGTGCCTTG       480
    46    V  P  V  I  I  A  R  T  D  H  I  I  V  K  E  G  S  S  A  L
         ATTAATTGCAGTGCTTATGGCTTTCCTGACCTAGAGTTTAAGTGGTATAATTCTGTTGGC       540
    66    I  N  C  S  A  Y  G  F  P  D  L  E  F  K  W  Y  N  S  V  G
         AAGCTGCTGAAAGAGATGGACGACGAGAAGGAGAAAGGAGGAGGAAAATGGCAAATGCTG       600
    86    K  L  L  K  E  M  D  D  E  K  E  K  G  G  G  K  W  Q  M  L
         GACGGTGGCCTCCTGAACATCACCAAGGTGTCTTTCTCAGACAGAGGTAAATACACATGT       660
    106   D  G  G  L  L  N  I  T  K  V  S  F  S  D  R  G  K  Y  T  C
         GTGGCATCTAACATCTATGGCACTATAAACAACACGGTGACACTGAGAGTCATCTTTACC       720
    126   V  A  S  N  I  Y  G  T  I  N  N  T  V  T  L  R  V  I  F  T
         TCTGGAGACATGGGCGTGTACTATATGGTGGTGTGCCTCGTGGCCTTCACCATAGTCATG       780
    146   S  G  D  M  G  V  Y  Y  M  V  V  C  L  V  A  F  T  I  V  M
         ATCCTCAACATCACCCGCCTGTGTATGATGAGCAGTCACCTAAAGAAGACTGAGAAAGCC       840
    166   I  L  N  I  T  R  L  C  M  M  S  S  H  L  K  K  T  E  K  A
         ATCAATGAGTTCTTTAGGACAGAAGGTGCAGAGAAGCTGCAGAAGGCTTTTGAGATTGCT       900
    186   I  N  E  F  F  R  T  E  G  A  E  K  L  Q  K  A  F  E  I  A
         AAACGCATCCCCATCATAACCTCAGCCAAAACTCTAGAACTTGCCAAAGTGACTCAGTTC       960
```

FIG. 3B

```
206 K   R   I   P   I   I   T   S   A   K   T   L   E   L   A   K   V   T   Q   F
    AAAACCATGGAATTTGCTAGGTACATTGAAGAGCTTGCCAGGAGCGTGCCCCTGCCTCCC              1020
226 K   T   M   E   F   A   R   Y   I   E   E   L   A   R   S   V   P   L   P   P
    CTCATCATGAACTGCAGGACGATCATGGAGGAGATCATGGAAGTAGTCGGGCTGGAGGAG              1080
246 L   I   M   N   C   R   T   I   M   E   E   I   M   E   V   V   G   L   E   E
    CAGGGGCAGAATTTTGTGAGGCATACCCCAGAAGGCCAGGAAGCCCCAGATAGGGACGAG              1140
266 Q   G   Q   N   F   V   R   H   T   P   E   G   Q   E   A   P   D   R   D   E
    GTATACACCATCCCCAACTCACTGAAGCGAAGTGAGTCCCCCACCGCTGACTCGGATGCT              1200
286 V   Y   T   I   P   N   S   L   K   R   S   E   S   P   T   A   D   S   D   A
    TCGTCATTGCATGAGCAGCCTCAGCAGATTGCCATCAAGGTTTCAGTTCACCCCCAGTCC              1260
306 S   S   L   H   E   Q   P   Q   Q   I   A   I   K   V   S   V   H   P   Q   S
    AAAAGGGATCATGTGGATGACCAGGAGGGAGGACACTTTGAGGTCAAAGATGAAGAGGAG              1320
326 K   R   D   H   V   D   D   Q   E   G   G   H   F   E   V   K   D   E   E   E
    ACAGAACCATCAGAGGAACATTCCCCAGAGACTGCAGAGCCTTCTACAGACATAACGACC              1380
346 T   E   P   S   E   E   H   S   P   E   T   A   E   P   S   T   D   I   T   T
    ACGGAGCTGACGTCCGAAGAGACGTCTCCTGTAGAGGCACCAGAACGAGGACTGCCACCA              1440
366 T   E   L   T   S   E   E   T   S   P   V   E   A   P   E   R   G   L   P   P
    GCACACCTAGAAACAACCGAGCCAGCAGTGACATGTGACAGAAACACCTGCATTATTTAT              1500
386 A   H   L   E   T   T   E   P   A   V   T   C   D   R   N   T   C   I   I   Y
    GAAAGCCATGTCTAAtcttaactccgaaaagcctatgcatatcaagaaaatcagggget              1560
406 E   S   H   V   *
``` gctccttaatacaaatgtagtatgcacttgccgctaagccttaccaggagacgctcatcccttaggtaagagtgatgcccctagagaggga
agacgcctgcatggagttcacgtgactggaatcaccccagtgaaaaggatctgaagagtgctggggtacagaactgataagatggagcaggg
gtctgtccgtgtgatctgaactgtagagaccattctctgccaaattccttaagtggtgatgccctttggccaagagtacactattgttgta
agacgttctgagttcaggagccctgtctagtgcgtactgcattgcttttccttggaaaattacaggtctgctacagtagcaaaggctcacac
atgggtttttaccactttgttgtcagtttgaattatcttcgccgttctttcctaatggagtagttgtttttatattaatattaattgctct
ttttgctggaatcttctgtgtcacctttgtccttatttttcctgagtagggtggacctcagagtcttgggtgtcacccactgacacagttga
tatctgtaagtcatatgtaatgctccaaagtagttactacacgccttttttattttccctaatttcctctttaaaaaaattaataacctcaca
tctattttcatagactttgtttccaatgaagctgctattgtgaaactgagaaaaactttgcccccagatagcactttaagagtcaaataa
<u>aaacgtttaccct</u>

FIG. 3C

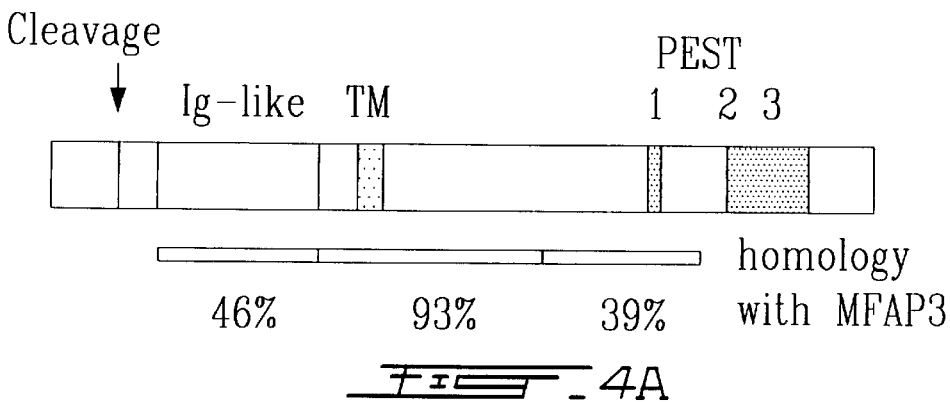

FIG. 4A

```
dft-A    1 MGLQKSHLTV CLPPSVP---------FLI LVSTLATAKS VTNSTLNGTD
MFAP3    1 .K.HCCLF.L VASII..AAFVLEDVD.DQ M..LE.NRS. YNA.FPSSFE
                                           * dft-A   41 VVLGSVPVII ARTDHIIVKE GSSALINCSA YGFPDLEFKW YNSVGKLLKE
MFAP3   50 LSAS.----H SDD.V..A.. .T.VS.E.LL TASHYEDVH. H..K.QQ.DG
                                                      * dft-A   91 MDDEKEKGGG KWQMLDGGLL NITKVSFSDR GKYTC-VASNI YGTINNTVTL
MFAP3   96 RSR-----.. ..-LVSDNF. ...N.A.D.. .L...F.T.P. RASY--S...

dft-A  141 RVIFTSGDMG VYYMVVCLVA FTIVMILNIT RLCMMSSHLK KTEKAINEFF
MFAP3  139 ........S ....I...I. ...TL...V. ........R ..........

dft-A  191 RTEGAEKLQK AFEIAKRIPI ITSAKTLELA KVTQFKTMEF ARYIEELARS
MFAP3  189 .......... .......... .......... .......... ..........

dft-A  241 VPLPPLIMNC RTIMEEIMEV VGLEEQGQNF VRHTPEGQEA PDRDEVYTIP
MFAP3  239 .......L.. .AFV..MF.A .RVDD-PDDL GERIK.RPAL NAQGGI.V.N
                         1 dft-A  291 NSLKRSESPT ADSDASSLHE QPQQIAIKVS VHPQS--KRDHV DDQEGGHFEV
MFAP3  288 PEMG..N..G G...DG..N. .G.E..VQ.. ...L..ET.SIDT ES.GSS...SP
                    2                    3 dft-A  341 KDEEETEPSE EHSPETAEPS TDITTTELTS EETSPVEAPE RGLPPAHLET
MFAP3  340 P.DIGSAE.N CNYKDG.YEN CQL dft-A  391 TEPAVTCDRN TCIIYESHV
```

FIG. 4B

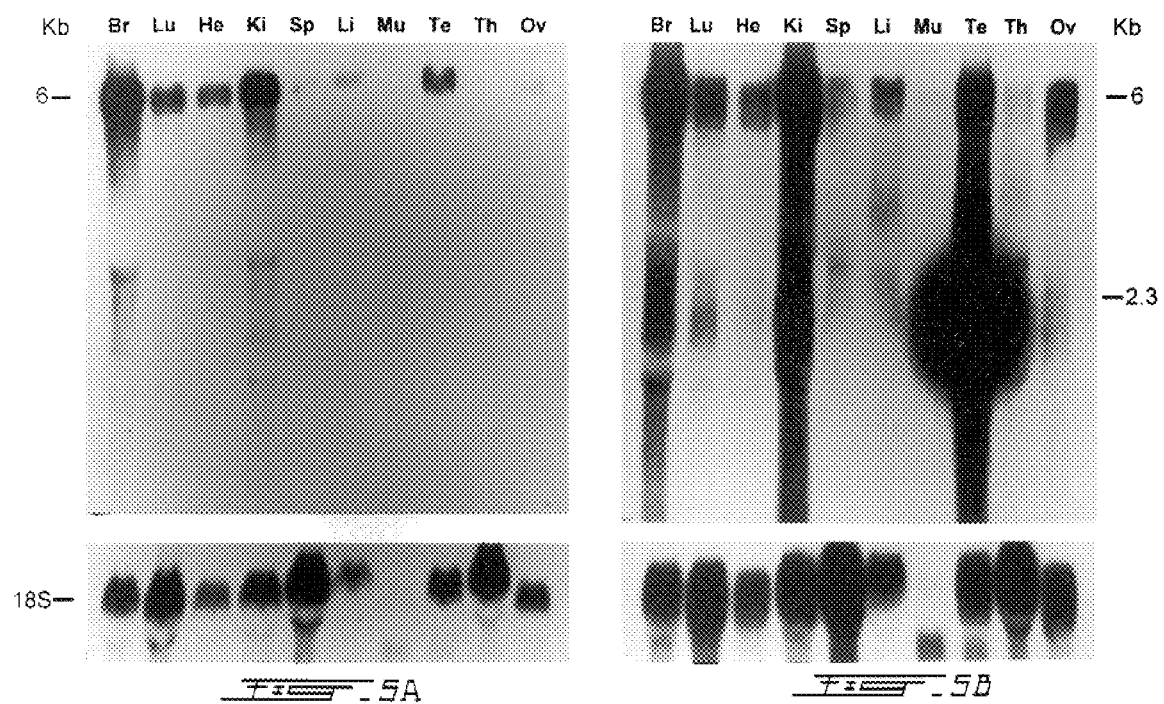

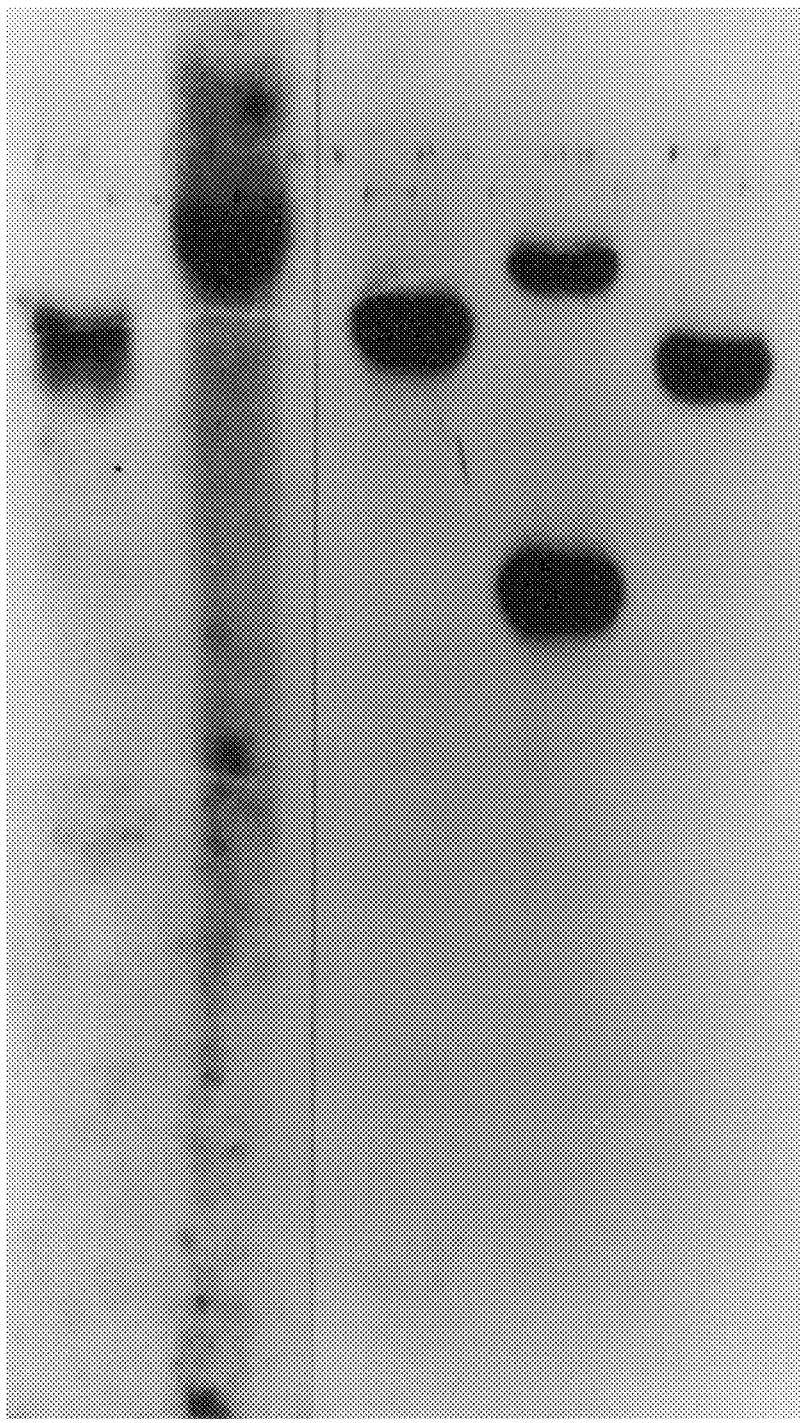

DFT-A GENE, DIAGNOSTIC AND THERAPEUTIC USES THEREOF

BACKGROUND OF THE INVENTION (a) Field of the Invention

The invention relates to one novel gene, dft-A, which is regulated by FOS and RAS transforming pathways, its diagnostic use and therapeutic use thereof.

(b) Description of Prior Art

Oncogenes represent activated variants of cellular proto-oncogenes whose products are essential in all aspects of cell signaling (cytokine, receptor, kinase and transcription factor). We have been interested in the transformation of rat-1 fibroblasts by v-fos, the oncogene of the FBJ murine sarcoma virus. The c-fos proto-oncogene itself can induce transformation if overexpressed and deleted of its 3' non-coding region. The Fos proteins have DNA-binding properties and they function as transcriptional activators after their dimerization with Jun proteins. Although several target genes of c-fos and v-fos have been identified, their mechanisms of transformation remain to be elucidated. In particular, most of the cellular effector gene products which are essential for the transformed state of the cells are unknown, although it seems likely that many effectors are responsible for all the modifications affecting transformed cells. One putative effector gene of v-fos transformation is fte-1. Other candidate effector genes for v-fos transformation have been recently proposed.

We used the mRNA Differential Display technique based on RT-PCR (or DDRT-PCR) to identify additional candidate effector genes of fos transformation and to test them in other transformed cells. The DDRT-PCR technique has been developed to rapidly clone genes whose expression are differentially regulated in two or more cell lines. This technique is based on the amplification of cDNA reflecting the relative abundance of mRNA from different cell lines.

It would be highly desirable to be provided with a gene regulated by FOS and RAS transforming pathways which could be used for the diagnostic and treatment of cancers.

SUMMARY OF THE INVENTION

One aim of the present invention is to provide one gene regulated by FOS and RAS transforming pathways which could be used for the diagnostic and treatment of cancers.

There is evidence presented here that a novel gene whose expression is upregulated in fos and v-Ha-ras transformed cells was cloned. This gene (dft-A) encodes a protein which is a member of the immunoglobulin (Ig) gene superfamily and contains one C2-type Ig-like domain and one potential transmembrane (TM) domain. In addition, this novel protein shares a region of high homology with the recently described microfibril-associated protein 3 (MFAP3) (Abrams, W. R. et al. (1995) *Genomics* 26:47–54).

In accordance with the present invention there is provided a gene regulated by FOS and RAS transforming pathways, which is identified as dft-A, and which comprises the sequence set forth in FIG. 3.

In accordance with the present invention there is provided a dft-A protein encoded by the dft-A gene of the present invention.

In accordance with the present invention there is provided an antibody which recognizes the protein of the present invention.

In accordance with the present invention there is provided a diagnostic method of identifying dft-A mutations in cancer or other diseases in a biological sample of a patient, which comprises:

a) subjecting DNA present in said patient's sample to gene sequencing; and b) comparing said sequenced DNA with the sequence of dft-A gene of the present invention to identify dft-A mutations.

In accordance with the present invention there is provided a diagnostic method of identifying change in dft-A protein level in cancer or other diseases in a biological sample of a patient, which comprises:

a) subjecting said patient's sample to the antibody of the present invention to form an antibody-dft-A protein complex; and b) detecting said antibody-dft-A protein complex to determine the dft-A protein level in said biological sample.

In accordance with the diagnostic method of the present invention, said other diseases may be neurological or CNS diseases.

In accordance with the present invention there is provided the use of the gene of the present invention for the treatment of axon guidance-related diseases in gene therapy protocol or by regulating dft-A activity.

The regulating may be effected by inhibiting dft-A activity.

The axon guidance-related diseases may be neurological or CNS diseases.

BRIEF DESCRIPTION OF THE DRAWINGS

FIG. 2 illustrates the expression of dft-A and dft-C/cyr61 in normal and transformed rat-1 cells;

FIG. 3 illustrates the sequence of the dft-A cDNA open reading frame (SEQ ID NOS:16–17);

FIGS. 4A and 4B illustrate the dft-A protein as a member of the Ig gene superfamily and as highly homologous to the MFAP3 protein (SEQ ID NO:18);

FIG. 5 illustrates the tissue-specific expression of dft-A in adult rat tissues; and FIG. 6 illustrates the conservation of dft-A sequences in mammalian species.

DETAILED DESCRIPTION OF THE INVENTION

Figure 1:
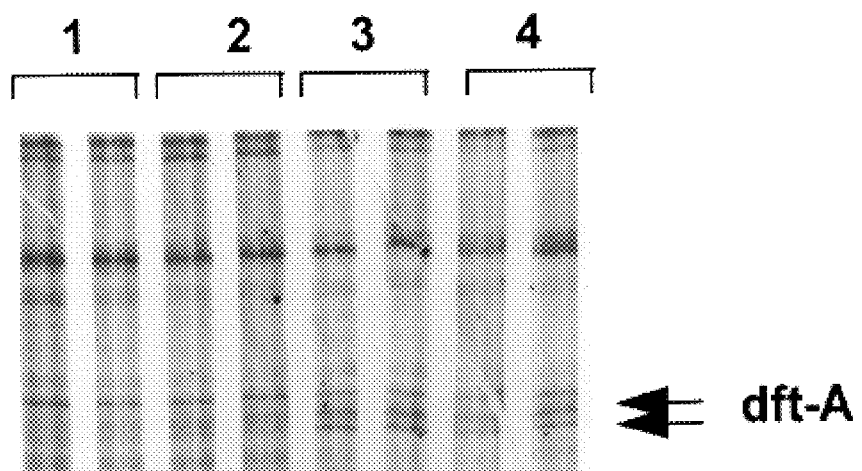
FIG. 1 illustrates the cDNA differential display of normal versus fos-transformed rat-1 cells.
Figure 1:
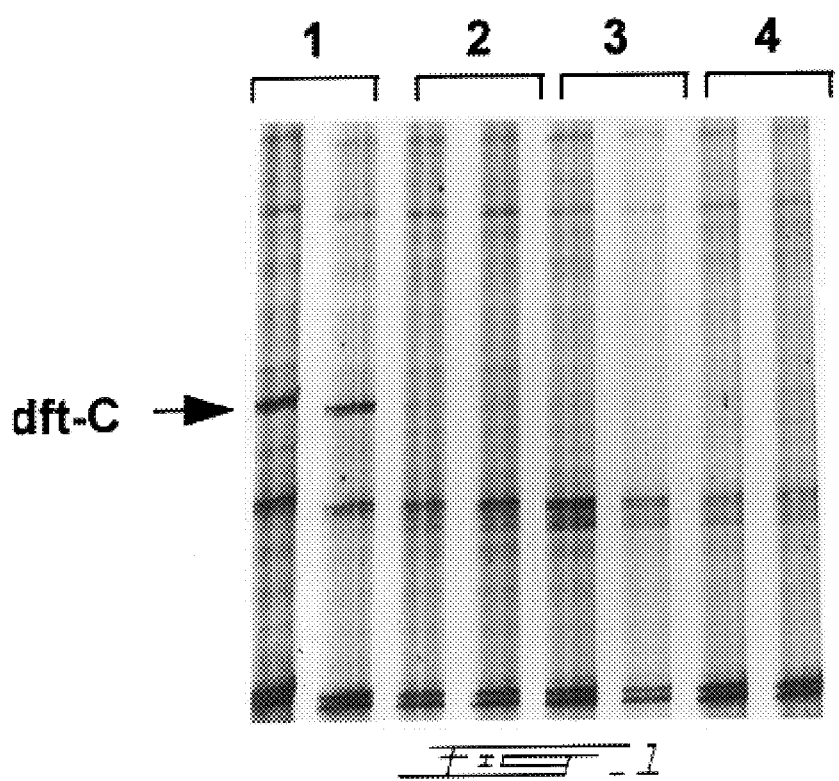

To search for novel effector genes of fos transformation, an mRNA differential display on normal versus fos-transformed rat-1 cells was performed. This analysis led to the identification of two genes dft-A and dft-C respectively upregulated and downregulated in fos (and in v-Ha-ras) transformed rat-1 cells but not in fos (or V-Ha-ras) revertant cells, indicating that these genes are regulated by the fos and ras transforming pathways.

Interestingly, the downregulated dft-C gene was found to be the rat homologue of the mouse immediate-early gene cyr61 which is suspected to be a cell—cell communication regulator.

In contrast, the sequence of the upregulated dft-A gene corresponds to a novel gene expressed in several adult rat tissues, and most abundantly in kidney, brain and testis. The predicted dft-A protein shares extensive homology with MFAP3, an extracellular protein associated with microfibrils. Furthermore, dft-A contains several motifs characteristics of the members of the immunoglobulin gene superfamily (signal peptide, one C2-type Ig-like and one potential transmembrane domain).

As predicted from their structure, these two putative effectors of fos transformation may influence cell morphology and cell-cell communication.

EXPERIMENTAL PROCEDURES

Cells

The LAP/cfos cell line, the v-fos transformed rat-1 cells and the EMS-1-17 cell line were previously described (Zarbl, H. et al. (1987) *Cell* 51:357–369; Balsalobre, A. et al. (1995) *Oncogene* 11:455–465). The 4NV clones were isolated from v-fos transformed rat-1 cells using a novel selection based on vincristine resistance. The v-ras and the v-src transformed rat-1 cells and the v-ras revertants have been derived in our lab. The v-Ha-ras and the v-src transformed rat-1 cells were obtained by infection with retroviruses and subsequent selection of foci. The v-Ha-ras revertants were obtained by selection of flat colonies after selection with pyronin y staining of EMS-treated v-Ha-ras transformed rat-1 cells. The rat-1 cells and the fos-expressing cells were maintained in Minimum Essential Medium supplemented with 10% calf serum (Gibco). The other cell lines were maintained in Dulbecco's Modified Eagle Medium supplemented with 5°/0 calf serum. The induction of LAP/cfos cells with IPTG was performed as described previously (Balsalobre, A. et al. (1995) *Oncogene* 11:455–465).

DDRT-PCR screening

The DDRT-PCR was performed as previously described (Okamoto, K. et al.(1994) *Embo Journal* 13:4816–4822), with minor modifications. For our screening, we used 10 different 5' primers and 2 anchored oligo dT primers. The sequences of these primers are the following: 5' primers: TCGAGGGCCA (SEQ ID NO:1), AGCTTGGCCC (SEQ ID NO:2), CGAAGGACGT (SEQ ID NO:3), CCTTCGAGCT (SEQ ID NO:4), CAAGCGAGCT (SEQ ID NO:5), AACGCGCMC (SEQ ID NO:6), GAGCTATGGC (SEQ ID NO:7), AGCCTGTGTC (SEQ ID NO:8), CTTGATTGCC (SEQ ID NO:9), CTGATCCATG (SEQ ID NO:10), GACCGCTTGT (SEQ ID NO:11), CAAACGTCGG (SEQ ID NO:12).

The dft-A fragment was amplified using (T)12CG and CTGATCCATG primers. The dft-C fragment was amplified using (T)12CG and GACCGCTTGT primers.

Screening of the cDNA libraries

The rat adult brain oligo dT-primed cDNA library was obtained from V. Giguere (McGill University, Montreal). The mouse fetal kidney (e18) random-primed cDNA library was provided by J. Pelletier (McGill University, Montreal). These library were plated, transferred onto nylon membrane and hybridized following standard procedures.

Nucleic acids analysis

High molecular weight DNA was prepared, digested, separated on 1% agarose gel, transferred onto nylon membrane and hybridized following already described procedures (Zarbl, H. et al. (1987) *Cell* 51:357–369). Total RNA was extracted as previously described. Total RNA (15 µg) was separated on denaturing-gel, transferred onto nylon membrane and hybridized. The cyr61-specific probe consisted of a 1.2 kbp fragment from 168 to 1347 of the published mouse cyr61 sequence. This fragment was obtained by RT-PCR with primers A (CCGGATCCTCCTGCGCGCCACMT) (SEQ ID NO:13) and B (TAG GAT CCC TGG AGG CAC TTA GTCC) (SEQ ID NO:14), and confirmed by sequencing.

Sequence analysis

All the fragments amplified from the DDRT-PCR screening were cloned into T-vector (Bluescript-derived) and sequenced with T3 and T7 primers and by using the dideoxynucleotide-chain termination procedure (T7 sequencing kit from Pharmacia Biotech and [$\alpha$-$^{35}$S]dATP from NEN Dupont). The cDNA clones obtained from the rat library ($\lambda$gtll) were subcloned into Bluescript-SK vector and their extremities were sequenced. Since the mouse cDNA library was cloned into $\lambda$ZAPII phage (Stratagene), the cDNA clones were directly excised in vivo within Bluescript-SK and sequenced. Progressive deletions into the cDNA clone a were performed from both extremities with exonuclease III. The resulting clones were then sequenced.

Computer-assisted analysis

Most of the analysis were done using GCG facilities: Program Manual for the Wisconsin Package, Version 8.1-UNIX, Genetics Computer Group, 575 Science Drive, Madison, Wis. 53711. Some analysis was also confirmed using the PC/gene facilities: PC/gene Release 6.85, Intelligenetics, 700 East El Camino Real, Mountain View, Calif. 94040. The comparison with updated protein-databases (Brookhaven Protein Data Bank, Swiss-Prot, PIR, CDS translations from GenBank) were performed at the NCBI using the Blast network service. The last search was done on Jun. 10, 1996.

RESULTS

Identification of differentially-expressed mRNA in normal versus fos-transformed rat-1 cells To avoid identifying genes reflecting only clonal variations, we used an inducible cell line, the LAP/cfos cell line, previously derived in our laboratory (Balsalobre, A. et al. (1995) *Oncogene* 11:455–465). These rat-1 fibroblasts have been transfected with the c-fos coding region under the control of a promoter inducible by IPTG. As shown previously, the levels of Fos proteins in these IPTG-induced cells was about 10 times higher than those in the uninduced cells (Balsalobre, A. et al. (1995) *Oncogene* 11:455–465). In addition, the induced cells exhibited a transformed phenotype after three days of induction and grew in soft agar, while the uninduced cells exhibited a normal non-transformed morphology (Balsalobre, A. et al. (1995) *Oncogene* 11:455–465).

In order to identify genes differentially expressed, we used RNA from control nontransformed rat-1 cells, uninduced LAP/cfos cells, induced LAP/cfos cells and v-fos transformed rat-1 cells. RNA was extracted from LAP/cfos cells after 5 days of induction to insure that the RNA was from cells that were completely transformed, thus increasing the likelihood of identifying effector genes involved in the transformed phenotype. We used 10 different 5' primers and 2 different anchored-oligo dT primers as described in Experimental Procedures. Out of these 20 combinations of primers, two fragments had a reproducible different cellular expression (FIG. 1).

The DDRT-PCR was performed as described in Experimental Procedures, using RNA from rat-1 (lane 1), uninduced LAP/cfos (lane 2), induced LAP/cfos (lane 3) and v-fos transformed (lane 4) rat-1 cells. Each cDNA preparation was amplified in duplicate by two independent PCR. The length of both dft-A and dft-C fragments was about 250 bp (as estimated from a sequencing reaction not shown).

They were designated genes Deregulated by FosTransformation A and C (dft-A and dft-C). The dft-A cDNA was upregulated in induced-LAP/cfos and in v-fos transformed cells as compared to uninduced and to parental rat-1 cells. This suggested that the Fos proteins may be a positive regulator of this gene. The dft-A fragment run as a doublet as it is often the case with this technique. We confirmed that the two fragments were identical by cloning them separately. In contrast, the dft-C cDNA was downregulated in uninduced and induced-LAP/cfos and in v-fos transformed cells, as compared to rat-1 cells. Since we have previously shown that the uninduced-LAP/cfos cells contain higher levels of c-Fos proteins than the parental rat-1 cells (Balsalobre, A. et al. (1995) *Oncogene* 11:455–465), this result suggested that the expression of dft-C was already inhibited by a small amount of Fos proteins.

We subsequently cloned the ~250 bp dft-A and dft-C fragments and used them as probes to insure that they were capable of detecting a transcript differentially expressed in the cell lines studied. Sequencing of these fragments revealed that the dft-A fragment represented a novel cDNA sequence and that the dft-C fragment was identical to the non-coding 3' end of the mouse cyr61 immediate-early gene (see below).

Analysis of the expression of dft-A and dft-C/cyr61 in normal, transformed and revertant cell lines To optimize the efficiency of the Northern blot analysis, longer probes specific for dft-A or dft-C/cyr61 were derived. The probe specific for dft-A was derived from cDNA clones described below. The dft-C/cyr61-specific probe consisted of the entire coding region derived by RT-PCR from its published sequence. To investigate whether the expression of dft-A and dft-C/cyr61 was regulated by Fos proteins, or was the result of cell transformation, we studied v-fos revertant cell lines (Zarbl, H. et al. (1987) *Cell* 51:357–369). These revertants, derived from v-fos transformed rat-1 cells, contain high levels of v-Fos proteins competent for transformation but exhibit a non-transformed phenotype presumably resulting from mutations in cellular effector genes which are essential for transformation. In addition, we studied the expression of the genes in v-Ha-rastransformed and v-src-transformed rat-1 cells and in v-ras-revertant cells.

The probe specific for dft-A detected 6 kb and 2.3 kb transcripts in the v-fos transformed cells (FIG. 2).

Northern blot analysis was performed with RNA from normal (lane 1) and v-fos transformed rat-1 cells (lane 4), uninduced LAP/c-fos (lane 2) and induced LAP/cfos (lane 3) cells, EMS-1-17 and three independent 4NV fos-revertant cell lines (lanes 5 to 8), the v-fos transformed clone 4NV47 (lane 9), v-ras transformed (lane 10) and two independent ras-revertant cell lines (lanes 11 and 12) and two independent v-src transformed cells (lanes 13 and 14). The same membrane was successively hybridized with a dft-A-specific probe (A), a cyr61-specific probe (B) and a 18S rRNA-specific probe (C). The phenotype of each cell line is indicated as normal (N) or transformed (T). The relative expression in each cell line (as compared with normal rat-1 cells) is indicated. The abundance of each message has been corrected for the amount of total (RNA (as determined in C). The sizes of the RNAs have been estimated from marker RNAs.

The expression of dft-A was increased 8-fold in v-fos transformed cells and 2-fold in the induced LAP/cfos cells as compared to the parental rat-1 cells (FIG. 2A, lanes 14). Interestingly, its expression was also elevated in v-ras transformed cells (3-fold, lane 10) but not in v-src transformed cells (lanes 13 and 14). Furthermore, its expression was at a normal low level in v-fos and v-ras revertant cells (lanes 5 to 8 and lanes 11 and 12), indicating that the upregulation of the dft-A gene was not directly dependent on Fos or Ras proteins but rather on fos- or ras-transformation. In addition, the v-fos transformed cell line 4NV47 which has been derived through the same isolation protocol as the 4NV revertants also exhibited higher levels of dft-A RNA (2-fold) (FIG. 2 lane 9).

As expected from the DDRT-PCR result, the expression of the dft-C/cyr61 gene was inhibited (5 to 20-fold) in v-fos transformed and in the LAP/cfos cells (FIG. 2B, lanes 1–4). This inhibition was even more pronounced in the v-ras transformed cells (100-fold) (lane 10) but was less evident in the v-src transformed cells (3 to 5-fold) (lane 13, 14). Interestingly, the expression of the dft-C/cyr61 was also dependent on fos and ras transforming pathways since the revertants expressed much higher levels than the parental transformed cells (lanes 5 to 8, and 11 and 12).

Therefore, both the dft-A and dft-C/cyr61 genes appear to be regulated by fos and ras transforming pathways.

Cloning and sequencing of the dft-A cDNA

To obtain full-length dft-A cDNA, we screened two cDNA libraries (from rat brain and mouse kidney) with the DDRT-PCR-derived 250 bp fragment. Three clones which together represented about 6 kbp of sequences were obtained (FIG. 3A).

Schematic representation and overlapping of the three cDNA clones isolated (FIG. 3A). The clones-C and -D have been isolated from a rat brain library as a single 3.5 kbp insert containing an internal EcoRI. The clones-A and -B have been obtained from a mouse kidney library. The open bar corresponds to the open reading frame (from nt 287 to nt 1517).

We confirmed that each of these 3 clones recognized the same transcript by Northern blot analysis and that they were encoded by a single gene as revealed by Southern blot analysis.

We first localized the open reading frame in clone-A, by sequencing the extremities of the three cDNA clones. Clone A, which corresponds to the 5' end of the mRNA, was then entirely sequenced in both directions (FIG. 3B).

Nucleotide (nt) sequence and deduced amino acid sequence of the 5' end of the mouse dft-A cDNA (clone-A) (FIG. 3B). Nucleotide and amino acid numbers are given in the right and left side, respectively. The internal putative polyadenylation site is underlined.

The first initiation codon, found at position 287, is surrounded by a perfect Kozak sequence. The length of the open reading frame is 1230 bp which corresponds to a polypeptide of 409 amino acid (act) residues. Interestingly, two polyadenylation signals (AAATAAA) (SEQ ID NO:15) were found. The first one at position 2291 was not followed by a poly(A) tail. The second site was found at the 3' end of the clone D. This site was followed by a poly(A) tail and corresponds to the polyadenylation site found in the dft-A fragment initially cloned by DDRT-PCR. This observation will be informative for the analysis of the tissue-specific expression of dft-A (below).

The predicted dft-A protein exhibits characteristics of a member of the immunoglobulin (Ig) superfamily The dft-A protein contains several predicted motifs and domains which are schematically illustrated in FIG. 4A.

Schematic representation of the motifs and domains found in the dft-A protein and of the homology between dft-A and MFAP3 proteins (FIG. 4A).

First, the hydrophobicity analysis predicted a N-terminal signal peptide. The potential cleavage site is located between Ala28 and Lys29, conforming to the (−3, −1) rule (von Heijne, G. (1986) *Nuc. Acids Res.* 14:4683–4690). The predicted cleaved polypeptide based on nucleotide sequence analysis contains 381 aa which corresponds to a molecular weight of 42.4 kDa. This protein is acidic with an isoelectric point of 4.76. Second, the dft-A protein contains one C2-type Ig-like domain from residues 54 to 129. There are 3 different subcategories of Ig-like domain: V-type, C1-type and C2-type (Williams, A. F. et al. (1988) *Annual Rev. of Immunol.* 6:381–405). These domains are present in proteins of the Ig superfamily. Proteins of the Ig superfamily usually contain many Ig-like domains but a few of them contain only one (CD3 contains one C2-type domain and the myelin protein Po contains one V-type domain). The Ig-like domain of dft-A falls in the C2-type category from the distance between the conserved cysteine residues (57 aa) and the presence of conserved residues (FIG. 4B).

Comparison of the amino acid sequence between the dft-A and MFAP3 proteins. Identical residues in MFAP3 are indicated as dots. Gaps introduced to optimize alignment are represented by dashes. The vertical arrow indicates the potential cleavage site between Ala28 and Lys29. The residues in bold are conserved in C2-type Ig-like domains. The two cysteines indicated with a star (*) are involved in the Ig-loop. The double underline indicates the potential TM segment and the underline indicates the three PEST regions.

Third, a single transmembrane segment spanning residues 151–167 can be predicted. Finally, the intracellular region contains 3 PEST regions of high scores (11.4, 23.3 and 31.7), respectively spanning residues 296–308, 342–351 a d 353380. These regions are thought to trigger rapid intracellular degradation of the protein containing them. As an example, the c-Myc protein contains 2 PEST regions with scores of 8.6 and 25.4. It can therefore be anticipated that the half-life of the dft-A protein will be short. It is noteworthy that many of the proteins involved in cell growth and differentiation do contain PEST sequences to maintain them at non-detrimental levels. Thus, dft-A appears to be a type I protein with an extracellular region containing an Ig-like domain, a TM region and a large intracellular region (from residues 168 to 409).

Although no stop codon was found in frame with, and upstream of the first methionine, it is very unlikely that the open reading frame starts more 5' for three main reasons. First, the first methionine was surrounded by a perfect Kozak sequence. Second. dft-A and the homologous MFAP3 (see below) are colinear, their C2-type Ig-like domains extending from their residues 50 to 125 and their highly conserved regions extending from the same residues, 135 to 250. This colinearity suggests that these two proteins have an overall conserved structure. Third, and most importantly, the N-terminal region of the predicted dft-A protein exhibits all the characteristics expected from a protein targeted to the secretory pathway. The dft-A protein has a hydrophobic N-terminal leader peptide that may function as a secretory signal and E potential cleavage site was found between residues 28 and 29.

Comparison of the deduced amino acid sequence of the dft-A protein with sequences in databases available from GCG facilities (see Experimental Procedures) revealed that it was most homologous to the microfibril-associated protein 3 (MFAP3) protein (FIG. 4B). The MFAP3 protein has recently been identified as a component of microfibrils (Abrams, W. R. et al. (1995) Genomics 26:47–54). A C2-type Ig-like domain is also present in MFAP3 (residue 59 to 130) and the homology of this domain with that of dft-A is 46%. dft-A and MFAP3 proteins also share extensive homology (93%) over 113 aa containing the putative TM domain, 13 aa of the extracellular domain most proximal to the TM domain and 83 aa of the intracellular portion most proximal to the TM domain. In addition, a good homology (about 42.5% identity) between dft-A and MFAP3 is found over another 144 aa around the first PEST domain. However, the first 59 aa and the last 85 aa of the dft-A sequences are totally divergent. Together, these results suggest that the dft-A protein belongs to the Ig gene superfamily.

dft-A expression in normal rat tissues

To obtain additional information about this novel dft-A gene, we investigated its expression in different adult rat tissues. In our first screening we used a 3' end probe which corresponds to non-coding sequences. Expression of the 6 kb dft-A transcript was detected at highest levels in brain, testis and kidney. This RNA species was also detectable at lower levels in lung, heart, spleen, liver, muscle and ovary (FIG. 5A).

Northern blot analysis was performed using RNA from adult rats. Filter was hybridized with the clone D which corresponds to the 3' end of the dft-A cDNA (A) or with a 1 kbp fragment of clone-A which corresponds to the 5' end of the dft-A cDNA (B). RNA were from brain (Br), lung (Lu), heart (He), kidney (Ki), spleen (Sp), live (Li), muscle (Mu), testis (Te), thymus (Th) and ovary (Ov). The filters were washed and rehybridized with a β-actin probe (bottom). The size of the RNAs was estimated from marker RNAs.

The 6 kb RNA in positive tissues was similar in size with the RNA found in v-Ha-ras transformed rat-1 cells (FIG. 2A lane 10).

We also hybridized the same RNA with a 5' end probe consisting of coding sequences. Surprisingly, a novel 2.3 kb RNA was detected most abundantly in testes (FIG. 5B lane 8) and in v-fos transformed rat-1 cells (FIG. 2A lane 4). The use of an alternative polyadenylation site at position 2291 in some cells may explain the production of the 2.3 kb RNA species. From Northern blot analysis using many small probes derived from the 3 cDNA clones, it seems that both transcripts contain the same open reading frame which is all included within the first 1.5 kbp of the clone A.

The dft-A gene is conserved

We examined whether the dft-A sequences were conserved between species by performing a Southern blot analysis with rat dft-A probe. As shown in FIG. 6, dft-A sequences were detected in several mammalian species, including mouse and human.

Southern blot analysis was performed with BamHI-digested DNAs from cow (Co), human (Hu), hamster (Ha), rat (Ra) and mouse (Mo). The hybridization was done with the rat dft-A cDNA probe (clone-D) at high stringency. Molecular weight markers are indicated in kbp.

DISCUSSION

Using the DDRT-PCR screening technique with 20 different combinations of primers, we identified two genes which are differentially regulated in normal versus fos (or Ha-ras) transformed rat-1 cells. Since one combination of primers allows the comparison of the expression of 50 to 100 mRNA (Liang, P. et al. (1992) Science 257:967–971), we can estimate that about 0.1 to 0.2% of the mRNAs are regulated by fos transformation. Interestingly, the two genes identified here encode proteins which are expressed outside the cell membrane either as a growth factor (Cyr61) or as a putative transmembrane protein (Dft-A). The use of fos and Ha-ras transformation revertant cells in the present study has represented a valuable tool for determining whether these putative effectors were directly dependent on the expression of the oncogene or whether they were dependent on the transforming pathway. Our results indicate that neither of these genes appear to be a direct target of the fos (or ras) protein since their regulation was not affected in non-transformed fos- or ras-revertant cells still expressing high levels of competent fos or ras proteins. Rather, these genes seem to be regulated by the transformed state of the cells.

Previous studies have reported the identification of other genes deregulated by fos transformation. Fte-1, a mammalian homologue of a yeast gene involved in protein import into mitochondria was induced to a modest level in v-fos transformed cells and was found to be required for this transformation. Hennigan et al. (Hennigan, R. F. et al. (1994) *Oncogene* 9:3591–3600) identified 10 genes [cathepsin L, Mts-1, p11 calpactin, p67 LBP, p35 Mac-2, EF-1 a, non-neuronal enolase, GAPDH, ribosomal protein S13, 2C9 (a novel gene)] which were differentially expressed between v-fos transformed and 208F non-transformed cells. Many of these were associated with invasion and metastasis. Joos and Müller (Jooss, K. U. et al. (1995) *Oncogene* 10:603–608) found that expression of the genes coding for ezrin and for tropomyosin-3 and -5 was elevated while that of tropomyosin-l was decreased in v-fos transformed cells as compared to normal 208F cells. Similarly, the Fit/T1/ST2 gene was identified in several screens, as exhibiting an induced expression by an activated Ha-ras or v-mos oncogene, as a serum-inducible gene in mouse fibroblasts and notably as a Fos-responsive gene in rat fibroblasts. As dft-A, the Fit/T1/ST2 protein is a member of the Ig gene superfamily. In contrast to dft-A which appears to be regulated by the Fos transformation state of the cells, the Fit/T1/ST2 gene seems to be a Fos-responsive gene. Interestingly, in a screen for genes differentially expressed between c-fos−/− et c-fos+/+ cells, a new member of the platelet-derived growth factor/vascular endothelial growth factor was identified as being significantly downregulated in c-fos deficient cells. Therefore, the two genes identified in our screen (cyr61 and dft-A) have not been previously associated with fos or Ha-ras transformation.

Is the downregulation of cyr61 playing a role in the transformation of rat-l cells by the fos and Ha-ras oncogenes?

The cyr61 gene was first identified as an immediate-early gene in serum-stimulated cells. The Cyr61 protein belongs to a family of extracellular proteins, including the Connective Tissue Growth Factor, Twisted gastrulation and Nov. The members of this family (the name CCN has been proposed for CTGF, Cyr61, Nov) have a very similar structure consisting of 4 distinct modules. The Cyr61 protein is associated with the extracellular matrix (ECM) and the cell surface and has been shown to promote cell attachment and spreading and growth factor-induced DNA synthesis. It is thought to be an ECM signaling molecule. The nov gene has been identified as the site of provirus integration in one nephroblastoma induced by an avian myeloblastosis-associated retrovirus and it has been shown to be overexpressed in many nephroblastomas. It has also been found that the expression of an N-terminal truncated form of nov induced the transformation of chicken embryo fibroblasts (CEF). Interestingly, expression of the normal nov gene in CEF had a marked inhibitory effect on their growth potential.

Moreover, it was recently reported that the expression of nov is downregulated in v-src transformed, in serum-stimulated quiescent and in proliferating CEF.

We also found that the expression of cyr61 was significantly (by 10-fold and ~100-fold) decreased in fos- and ras-transformed cells, respectively, suggesting that this downregulation may be required for or may be an important component of this process. The ability of normal nov (a member of the same family as cyr61) to inhibit cell growth and the capacity of cyr61 to promote cell attachment would be compatible with a role in cellular transformation. Moreover, the fact that cyr61 is rapidly induced in serum-stimulated normal cells could be interpreted as a negative feedback to limit cell growth. Therefore, a downregulation of cyr61 would be expected to decrease cell attachment and favor a more malignant phenotype of transformed cells.

The dft-A gene encodes a novel member of the immunoglobulin gene superfamily and is a putative effector for v-Ha-ras and fos transformation The dft-A gene was found to be upregulated to modest levels (3- to 8-fold) in fos- and Ha-ras transformed cells. The gene is novel and encodes a 409 amino acid residue protein which shows homology with members of the Ig gene superfamily, and specifically with MFAP3. The MFAP3 protein has been identified as a component of the microfibrils which are either associated with elastin or constitute an important component of the ECM of several tissues (Abrams, W. R. et al. (1995) *Genomics* 26:47–54). Little is known about the MFAP3 gene product. Functional studies on the MFAP3 protein have not yet been reported and it is unknown whether it plays other non-structural role. The homology between the dft-A and the MFAP3 proteins is very high (93%) in the central portion of the molecule, suggesting that this region may have the same function in both proteins and possibly interact with the same putative effectors. As a component of microfibrils, MFAP3 is thought to be a secreted protein. However, the dft-A protein is more structurally related to a transmembrane than to a secreted protein. Our analysis revealed that the region of dft-A spanning residues 151–167 has a high probability of being a TM segment. Moreover, this putative TM region is located downstream (about 25 amino acids) of the Ig-like domain, as usually found in other proteins of the Ig gene superfamily which are almost all transmembrane proteins. However, the high homology of dft-A with MFAP3, especially in the region of and surrounding the putative TM domain and the localization of MFAP3 to microfibrils suggest that the dft-A protein may also be secreted. Further work will be needed to clarify this issue.

Among the members of the Ig gene superfamily, some are involved in cell-cell adhesion and belong to the family of cell adhesion molecules (CAM). Although we have not yet studied whether the dft-A protein exhibit adhesion properties, it is possible that it belongs to the CAM family. These Ig-like-containing CAMs can be structurally divided into subfamilies whose members have the same number of domains (Cunningham, B. A. (1995) *Current Opinion in Cell Biology* 7:628–633). As a putative Ig-like CAM, dft-A would belong to the n/O subfamily characterized by the absence of the fibronectin type III domain (another domain found in CAM). In this n/O subfamily, another number (Po) harbors a single Ig-like domain as dft-A.

The upregulation of the dft-A gene expression in fos and Ha-ras transformed cells and its structure (as a member of the Ig gene superfamily and possibly as a member of the CAM gene family) suggest that dft-A may be involved in cell transformation. Several molecules belonging to the Ig gene superfamily have been implicated in tumorigenesis and cancer metastasis (Johnson, J. P. (1991) Cancer &. Metastasis Reviews. 10:11–22). Expression of some of them (DCC, biliary glycoprotein) seem to inhibit tumor cell growth, while expression of several others appears to be associated with a more malignant phenotype. For example, the carcinoembryonic antigen found to be overexpressed in many human cancers can induce metastasis of Chinese hamster ovary cells and collaborate with myc and B-cl-2 for transformation in vitro. The A33 and pE4/TuAg.1 tumor antigens are overexpressed respectively in human colon cancer and in rat colon and mammary carcinoma relative to normal tissues. The B-CAM protein is up-regulated following transformation in some cell types and may contribute to this phenotype. Indeed, B-CAM is homologous to MCAM/MUC18, a tumor marker for human melanoma, whose expression correlates with tumor progression. Moreover, MCAM/MUC18 has recently been reported to significantly increase the tumorigenic potential of MCAM/MUC18-negative SB-2 melanoma cells. N-CAM has been implicated in tissue cell invasion. Similarly, the levels of expression of 1-CAM in melanoma cells were found to correlate with their metastatic potential. Finally, PE-CAM, a molecule expressed on normal endothelial cells, was found to be expressed in solid tumor cells and to be implicated in adhesion of tumor cells to endothelium.

Like many of these molecules which belong to the Ig gene superfamily, dft-A is a novel cell surface receptor or CAM and may also be implicated in tumorigenesis.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The embodiments of the invention in which an exclusive property or privilege is claimed are defined as follows:

1. An isolated DNA molecule comprising a DNA sequence consisting of SEQ ID. NO:16, which is identified as dft-A.

* * * * *

```
                          SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

TCGAGGGCCA                                                              10

(2) INFORMATION FOR SEQ ID NO:2:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

AGCTTGGCCC                                                              10

(2) INFORMATION FOR SEQ ID NO:3:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

CGAAGGACGT                                                              10

(2) INFORMATION FOR SEQ ID NO:4:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: cDNA
```

(xi) SEQUENCE DESCRIPTION: SEQ ID NO:4:

CCTTCGAGCT                                                                 10

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CAAGCGAGCT                                                                 10

(2) INFORMATION FOR SEQ ID NO:6:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AACGCGCMC                                                                  9

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GAGCTATGGC                                                                 10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AGCCTGTGTC                                                                 10

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CTTGATTGCC                                                                 10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

CTGATCCATG                                                              10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GACCGCTTGT                                                              10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CAAACGTCGG                                                              10

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCGGATCCTC CTGCGCGCCA CMT                                               23

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TAGGATCCCT GGAGGCACTT AGTCC                                             25

(2) INFORMATION FOR SEQ ID NO:15:

-continued

```
    (i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

AAATAAA                                                               7

(2) INFORMATION FOR SEQ ID NO:16:

(i) SEQUENCE CHARACTERISTICS:
        (A) LENGTH: 2309 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 287...1513
        (D) OTHER INFORMATION:
        (A) NAME/KEY: polyA_site
        (B) LOCATION: 2290...2297
        (D) OTHER INFORMATION:

(xi) SEQUENCE DESCRIPTION: SEQ ID NO:16:

GGAAGCTCCG GCTCCCGGCG GCGGGGCTCG TAACCCGCAT CGAGAAGAGG CGCGGGCGGC     60

GGAGGAGGTT GGTACACGCT CGGTCCTGCA GAGCTCCCCG GGTGGCCATG GCGAGAGGTG    120

CACGGCGACC ACCCGAGTGG CGCAGCGGTG TCAGATTCTT CTTGAACAAG TACCAACTCC    180

ATGGATCCAG GACAGGTTTG TCCCATGGCC TGCTCTGAGC AGTGTGCAGT CTGAGAGAAG    240

ATTCCATTGG CAAACCATCT CTGGCCTTAC GGAACAAGCA AAGACG ATG GGT CTT       295
                                                  Met Gly Leu
                                                    1

CAG AAG AGC CAT CTG ACT GTG TGT TTA CCA CCT TCT GTG CCC TTC TTA      343
Gln Lys Ser His Leu Thr Val Cys Leu Pro Pro Ser Val Pro Phe Leu
      5                  10                  15

ATC CTA GTA TCC ACT CTA GCC ACT GCT AAG AGT GTG ACC AAC AGC ACT      391
Ile Leu Val Ser Thr Leu Ala Thr Ala Lys Ser Val Thr Asn Ser Thr
 20                  25                  30                  35

TTA AAT GGC ACT GAT GTG GTC TTG GGC TCT GTG CCC GTA ATC ATT GCC      439
Leu Asn Gly Thr Asp Val Val Leu Gly Ser Val Pro Val Ile Ile Ala
                 40                  45                  50

AGA ACT GAC CAT ATC ATA GTC AAA GAG GGG AGC AGT GCC TTG ATT AAT      487
Arg Thr Asp His Ile Ile Val Lys Glu Gly Ser Ser Ala Leu Ile Asn
             55                  60                  65

TGC AGT GCT TAT GGC TTT CCT GAC CTA GAG TTT AAG TGG TAT AAT TCT      535
Cys Ser Ala Tyr Gly Phe Pro Asp Leu Glu Phe Lys Trp Tyr Asn Ser
         70                  75                  80

GTT GGC AAG CTG CTG AAA GAG ATG GAC GAC GAG AAG GAG AAA GGA GGA      583
Val Gly Lys Leu Leu Lys Glu Met Asp Asp Glu Lys Glu Lys Gly Gly
     85                  90                  95

GGA AAA TGG CAA ATG CTG GAC GGT GGC CTC CTG AAC ATC ACC AAG GTG      631
Gly Lys Trp Gln Met Leu Asp Gly Gly Leu Leu Asn Ile Thr Lys Val
100                 105                 110                 115

TCT TTC TCA GAC AGA GGT AAA TAC ACA TGT GTG GCA TCT AAC ATC TAT      679
Ser Phe Ser Asp Arg Gly Lys Tyr Thr Cys Val Ala Ser Asn Ile Tyr
                 120                 125                 130

GGC ACT ATA AAC AAC ACG GTG ACA CTG AGA GTC ATC TTT ACC TCT GGA      727
Gly Thr Ile Asn Asn Thr Val Thr Leu Arg Val Ile Phe Thr Ser Gly
```

-continued

```
                       135                 140                 145
GAC ATG GGC GTG TAC TAT ATG GTG GTG TGC CTC GTG GCC TTC ACC ATA        775
Asp Met Gly Val Tyr Tyr Met Val Val Cys Leu Val Ala Phe Thr Ile
            150                 155                 160

GTC ATG ATC CTC AAC ATC ACC CGC CTG TGT ATG ATG AGC AGT CAC CTA        823
Val Met Ile Leu Asn Ile Thr Arg Leu Cys Met Met Ser Ser His Leu
    165                 170                 175

AAG AAG ACT GAG AAA GCC ATC AAT GAG TTC TTT AGG ACA GAA GGT GCA        871
Lys Lys Thr Glu Lys Ala Ile Asn Glu Phe Phe Arg Thr Glu Gly Ala
180                 185                 190                 195

GAG AAG CTG CAG AAG GCT TTT GAG ATT GCT AAA CGC ATC CCC ATC ATA        919
Glu Lys Leu Gln Lys Ala Phe Glu Ile Ala Lys Arg Ile Pro Ile Ile
                200                 205                 210

ACC TCA GCC AAA ACT CTA GAA CTT GCC AAA GTG ACT CAG TTC AAA ACC        967
Thr Ser Ala Lys Thr Leu Glu Leu Ala Lys Val Thr Gln Phe Lys Thr
            215                 220                 225

ATG GAA TTT GCT AGG TAC ATT GAA GAG CTT GCC AGG AGC GTG CCC CTG       1015
Met Glu Phe Ala Arg Tyr Ile Glu Glu Leu Ala Arg Ser Val Pro Leu
    230                 235                 240

CCT CCC CTC ATC ATG AAC TGC AGG ACG ATC ATG GAG GAG ATC ATG GAA       1063
Pro Pro Leu Ile Met Asn Cys Arg Thr Ile Met Glu Glu Ile Met Glu
245                 250                 255

GTA GTC GGG CTG GAG GAG CAG GGG CAG AAT TTT GTG AGG CAT ACC CCA       1111
Val Val Gly Leu Glu Glu Gln Gly Gln Asn Phe Val Arg His Thr Pro
260                 265                 270                 275

GAA GGC CAG GAA GCC CCA GAT AGG GAC GAG GTA TAC ACC ATC CCC AAC       1159
Glu Gly Gln Glu Ala Pro Asp Arg Asp Glu Val Tyr Thr Ile Pro Asn
                280                 285                 290

TCA CTG AAG CGA AGT GAG TCC CCC ACC GCT GAC TCG GAT GCT TCG TCA       1207
Ser Leu Lys Arg Ser Glu Ser Pro Thr Ala Asp Ser Asp Ala Ser Ser
            295                 300                 305

TTG CAT GAG CAG CCT CAG CAG ATT GCC ATC AAG GTT TCA GTT CAC CCC       1255
Leu His Glu Gln Pro Gln Gln Ile Ala Ile Lys Val Ser Val His Pro
    310                 315                 320

CAG TCC AAA AGG GAT CAT GTG GAT GAC CAG GAG GGA GGA CAC TTT GAG       1303
Gln Ser Lys Arg Asp His Val Asp Asp Gln Glu Gly Gly His Phe Glu
325                 330                 335

GTC AAA GAT GAA GAG GAG ACA GAA CCA TCA GAG GAA CAT TCC CCA GAG       1351
Val Lys Asp Glu Glu Glu Thr Glu Pro Ser Glu Glu His Ser Pro Glu
340                 345                 350                 355

ACT GCA GAG CCT TCT ACA GAC ATA ACG ACC ACG GAG CTG ACG TCC GAA       1399
Thr Ala Glu Pro Ser Thr Asp Ile Thr Thr Thr Glu Leu Thr Ser Glu
                360                 365                 370

GAG ACG TCT CCT GTA GAG GCA CCA GAA CGA GGA CTG CCA CCA GCA CAC       1447
Glu Thr Ser Pro Val Glu Ala Pro Glu Arg Gly Leu Pro Pro Ala His
            375                 380                 385

CTA GAA ACA ACC GAG CCA GCA GTG ACA TGT GAC AGA AAC ACC TGC ATT       1495
Leu Glu Thr Thr Glu Pro Ala Val Thr Cys Asp Arg Asn Thr Cys Ile
    390                 395                 400

ATT TAT GAA AGC CAT GTC TAATCTTAAC TCCGAAAAGC CTATGCATAT              1543
Ile Tyr Glu Ser His Val
        405

CAAGAAAATC AGGGGCTGCT CCTTAATACA AATGTAGTAT GCACTTGCCG CTAAGCCTTA     1603

CCAGGAGACG CTCATCCCTT AGGTAAGAGT GATGCCCCCT AGAGAGGGAA GACGCCTGCA     1663

TGGAGTTCAC GTGACTGGAA TCACCCCAGT GAAAAGGATC TGAAGAGTGC TGGGGTACAG     1723

AACTGATAAG ATGGAGCAGG GGTCTGTCCG TGTGATCTGA ACTGTAGAGA CCATTCTCTG     1783

CCAAATTCCT TAAGTGGTGA TGCCCTTTTG GCCAAGAGTA CACTATTGTT GTAAGACGTT     1843
```

| | |
|---|---|
| CTGAGTTCAG GAGCCCTGTC TAGTGCGTAC TGCATTGCTT TTCCTTGGAA AATTACAGGT | 1903 |
| CTGCTACAGT AGCAAAGGCT CACACATGGG TTTTTTACCA CTTTGTTGTC AGTTTGAATT | 1963 |
| ATCTTCGCCG TTCTTTCCTA ATGGAGTAGT TGTTTTTATA TTAATATTAA TTGCTCTTTT | 2023 |
| TGCTGGAATC TTCTGTGTCA CCTTTGTCCT TATTTTCCCT GAGTAGGGTG GACCTCAGAG | 2083 |
| TCTTGGGTGT CACCCACTGA CACAGTTGAT ATCTGTAAGT CATATGTAAT GCTCCAAAGT | 2143 |
| AGTTACTACA CGCCTTTTTA TTTTCCCTAA TTTCCTCTTT AAAAAAATTA ATAACCTCAC | 2203 |
| ATCTATTTTT CATAGACTTT TGTTTCCAAT GAAGCTGCTA TTGTGAAACT GAGAAAAACT | 2263 |
| TTGCCCCCAG ATAGCACTTT AAGAGTCAAA TAAAAACGTT TACCCT | 2309 |

(2) INFORMATION FOR SEQ ID NO:17:

(i) SEQUENCE CHARACTERISTICS:
        (A) LENGTH: 409 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:17:

```
Met Gly Leu Gln Lys Ser His Leu Thr Val Cys Leu Pro Pro Ser Val
  1               5                  10                  15

Pro Phe Leu Ile Leu Val Ser Thr Leu Ala Thr Ala Lys Ser Val Thr
             20                  25                  30

Asn Ser Thr Leu Asn Gly Thr Asp Val Val Leu Gly Ser Val Pro Val
         35                  40                  45

Ile Ile Ala Arg Thr Asp His Ile Ile Val Lys Glu Gly Ser Ser Ala
     50                  55                  60

Leu Ile Asn Cys Ser Ala Tyr Gly Phe Pro Asp Leu Glu Phe Lys Trp
 65                  70                  75                  80

Tyr Asn Ser Val Gly Lys Leu Lys Glu Met Asp Asp Glu Lys Glu
                 85                  90                  95

Lys Gly Gly Gly Lys Trp Gln Met Leu Asp Gly Gly Leu Leu Asn Ile
                100                 105                 110

Thr Lys Val Ser Phe Ser Asp Arg Gly Lys Tyr Thr Cys Val Ala Ser
            115                 120                 125

Asn Ile Tyr Gly Thr Ile Asn Asn Thr Val Thr Leu Arg Val Ile Phe
        130                 135                 140

Thr Ser Gly Asp Met Gly Val Tyr Tyr Met Val Val Cys Leu Val Ala
145                 150                 155                 160

Phe Thr Ile Val Met Ile Leu Asn Ile Thr Arg Leu Cys Met Met Ser
                165                 170                 175

Ser His Leu Lys Lys Thr Glu Lys Ala Ile Asn Glu Phe Phe Arg Thr
            180                 185                 190

Glu Gly Ala Glu Lys Leu Gln Lys Ala Phe Glu Ile Ala Lys Arg Ile
        195                 200                 205

Pro Ile Ile Thr Ser Ala Lys Thr Leu Glu Leu Ala Lys Val Thr Gln
    210                 215                 220

Phe Lys Thr Met Glu Phe Ala Arg Tyr Ile Glu Glu Leu Ala Arg Ser
225                 230                 235                 240

Val Pro Leu Pro Pro Leu Ile Met Asn Cys Arg Thr Ile Met Glu Glu
                245                 250                 255
```

```
Ile Met Glu Val Val Gly Leu Glu Glu Gln Gly Gln Asn Phe Val Arg
            260                 265                 270

His Thr Pro Glu Gly Gln Glu Ala Pro Asp Arg Asp Glu Val Tyr Thr
            275                 280                 285

Ile Pro Asn Ser Leu Lys Arg Ser Glu Ser Pro Thr Ala Asp Ser Asp
            290                 295                 300

Ala Ser Ser Leu His Glu Gln Pro Gln Gln Ile Ala Ile Lys Val Ser
305                 310                 315                 320

Val His Pro Gln Ser Lys Arg Asp His Val Asp Asp Gln Glu Gly Gly
            325                 330                 335

His Phe Glu Val Lys Asp Glu Glu Thr Glu Pro Ser Glu Glu His
            340                 345                 350

Ser Pro Glu Thr Ala Glu Pro Ser Thr Asp Ile Thr Thr Glu Leu
            355                 360                 365

Thr Ser Glu Glu Thr Ser Pro Val Glu Ala Pro Glu Arg Gly Leu Pro
            370                 375                 380

Pro Ala His Leu Glu Thr Thr Glu Pro Ala Val Thr Cys Asp Arg Asn
385                 390                 395                 400

Thr Cys Ile Ile Tyr Glu Ser His Val
            405

(2) INFORMATION FOR SEQ ID NO:18:

(i) SEQUENCE CHARACTERISTICS:
        (A) LENGTH: 362 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

Met Lys Leu His Cys Cys Leu Phe Thr Leu Val Ala Ser Ile Ile Val
1               5                   10                  15

Pro Ala Ala Phe Val Leu Glu Asp Val Asp Phe Asp Gln Met Val Ser
            20                  25                  30

Leu Glu Ala Asn Arg Ser Ser Tyr Asn Ala Ser Phe Pro Ser Ser Phe
            35                  40                  45

Glu Leu Ser Ala Ser Ser His Ser Asp Asp Val Ile Ile Ala Lys
50                  55                  60

Glu Gly Thr Ser Val Ser Ile Glu Cys Leu Leu Thr Ala Ser His Tyr
65                  70                  75                  80

Glu Asp Val His Trp His Asn Ser Lys Gly Gln Gln Leu Asp Gly Arg
            85                  90                  95

Ser Arg Gly Gly Lys Trp Leu Val Ser Asp Asn Phe Leu Asn Ile Thr
            100                 105                 110

Asn Val Ala Phe Asp Asp Arg Gly Leu Tyr Thr Cys Phe Val Thr Ser
            115                 120                 125

Pro Ile Arg Ala Ser Tyr Ser Val Thr Leu Arg Val Ile Phe Thr Ser
            130                 135                 140

Gly Asp Met Ser Val Tyr Tyr Met Ile Val Cys Leu Ile Ala Phe Thr
145                 150                 155                 160

Ile Thr Leu Ile Leu Asn Val Thr Arg Leu Cys Met Met Ser Ser His
            165                 170                 175

Leu Arg Lys Thr Glu Lys Ala Ile Asn Glu Phe Phe Arg Thr Glu Gly
            180                 185                 190
```

-continued

```
Ala Glu Lys Leu Gln Lys Ala Phe Glu Ile Ala Lys Arg Ile Pro Ile
        195                 200                 205
Ile Thr Ser Ala Lys Thr Leu Glu Leu Ala Lys Val Thr Gln Phe Lys
        210                 215                 220
Thr Met Glu Phe Ala Arg Tyr Ile Glu Glu Leu Ala Arg Ser Val Pro
225                     230                 235                 240
Leu Pro Pro Leu Ile Leu Asn Cys Arg Ala Phe Val Glu Glu Met Phe
                245                 250                 255
Glu Ala Val Arg Val Asp Asp Pro Asp Asp Leu Gly Glu Arg Ile Lys
                260                 265                 270
Glu Arg Pro Ala Leu Asn Ala Gln Gly Gly Ile Tyr Val Ile Asn Pro
        275                 280                 285
Glu Met Gly Arg Ser Asn Ser Pro Gly Gly Asp Ser Asp Asp Gly Ser
        290                 295                 300
Leu Asn Glu Gln Gly Gln Glu Ile Ala Val Gln Val Ser Val His Leu
305                     310                 315                 320
Gln Ser Glu Thr Lys Ser Ile Asp Thr Glu Ser Gln Gly Ser Ser His
                325                 330                 335
Phe Glu Pro Pro Asp Asp Ile Gly Ser Ala Glu Ser Asn Cys Asn Tyr
                340                 345                 350
Lys Asp Gly Ala Tyr Glu Asn Cys Gln Leu
                355                 360
```